(12) United States Patent
Jones

(10) Patent No.: US 8,839,674 B2
(45) Date of Patent: Sep. 23, 2014

(54) ULTRASONIC TESTING APPARATUS

(75) Inventor: Terence Jones, Bristol (GB)

(73) Assignee: Airbus Operations Limited, Bristol (GB)

( * ) Notice: Subject to any disclaimer, the term of this patent is extended or adjusted under 35 U.S.C. 154(b) by 538 days.

(21) Appl. No.: 12/656,127

(22) Filed: Jan. 19, 2010

(65) Prior Publication Data

US 2010/0206081 A1 Aug. 19, 2010

(30) Foreign Application Priority Data

Jan. 19, 2009 (GB) .................................. 0900767.5

(51) Int. Cl.
*G01N 29/24* (2006.01)
*G01N 29/22* (2006.01)
*G01N 29/04* (2006.01)

(52) U.S. Cl.
CPC ...... *G01N 29/043* (2013.01); *G01N 2291/0231* (2013.01); *G01N 29/225* (2013.01); *G01N 2291/106* (2013.01); *G01N 2291/2694* (2013.01); *G01N 2291/0258* (2013.01)
USPC .......................................... 73/641; 73/866.5

(58) Field of Classification Search
USPC ........ 73/866.5, 618, 619, 621, 633, 634, 641, 73/644
See application file for complete search history.

(56) References Cited

U.S. PATENT DOCUMENTS

| | | | |
|---|---|---|---|
| 3,121,326 A * | 2/1964 | Klatchko | 73/633 |
| 3,175,106 A * | 3/1965 | Sansom et al. | 310/336 |
| 4,322,975 A | 4/1982 | Schmidt et al. | |
| 5,447,070 A * | 9/1995 | Patzke et al. | 73/621 |
| 5,522,265 A * | 6/1996 | Jaeggi | 73/625 |
| 5,974,889 A * | 11/1999 | Trantow | 73/624 |
| 2004/0083815 A1* | 5/2004 | Lam et al. | 73/618 |
| 2005/0126293 A1* | 6/2005 | Dasch | 73/618 |

FOREIGN PATENT DOCUMENTS

| | | | |
|---|---|---|---|
| EP | 60952 A2 * | 9/1982 | |
| GB | 1 511 350 | 5/1978 | |

OTHER PUBLICATIONS

GB Search Report for 0900767.5 dated Apr. 30, 2009.

* cited by examiner

*Primary Examiner* — Peter Macchiarolo
*Assistant Examiner* — Rose M Miller
(74) *Attorney, Agent, or Firm* — Nixon & Vanderhye P.C.

(57) ABSTRACT

Ultrasonic testing apparatus including a base member having an aperture formed therein and a search member arranged to be rotatably received in the aperture of the base member and having at least one array aperture arranged to receive an ultrasonic array holder.

19 Claims, 3 Drawing Sheets

ULTRASONIC TESTING APPARATUS

Figure 1:
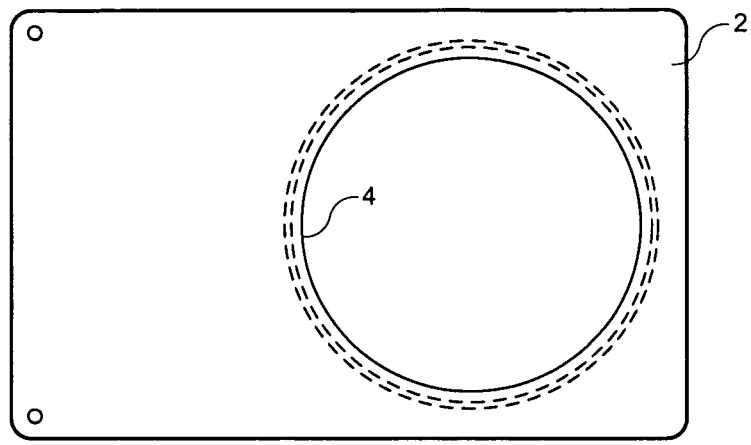

This application claims priority to GB Patent Application No. 0900767.5 filed 19 Jan. 2009, the entire contents of which is hereby incorporated by reference.

Non-destructive testing is an established technique of testing structures and materials for internal defects that are not visible using visual inspection techniques. One particular form of non-destructive testing is the use of one or more ultrasonic arrays to direct ultrasonic energy into the structure being tested and by analysing the characteristics of the returned ultrasonic energy determine if an internal fault is present in the structure or not.

One application for ultrasonic testing is in the aerospace industry in which it is desirable to test the integrity of various aircraft structures both during manufacture and as part of an ongoing maintenance program. In particular, ultrasonic testing is used to locate defects that have formed internally in a structure, such as internal fatigue cracking in metallic structures or cracking or delamination failures in fibre reinforced composite structures. An example of a particular structure that is susceptible to the formation of internal defects is the attachment point between the outer skin of an aircraft section and an underlying structural component such as a wing rib or stringer. Such a typical attachment point includes a fixing bolt that passes through aligned holes formed in both the top skin and rib or stringer and which is designed to be flush with the upper surface of the wing skin. Defects in both the top skin or rib typically form around the circumference of the holes through which the fixing bolt passes. It is important that any such defects are located either during manufacture or as part of a routine maintenance program.

Current ultrasonic testing methods to detect the presence of any defects around such a skin fastener require an ultrasonic array to be manually moved around the circumference of the recessed fastener. To achieve useful results it is highly desirable for the ultrasonic transducer to be maintained at a fixed angle relative to a radius of the fastener as the ultrasonic array is moved circumferentially around the fastener. This is relatively difficult to do manually whilst also ensuring that the ultrasonic array is moved smoothly at a substantially constant speed. Consequently, to achieve reliable test results a skilled and well trained operative is required. It would clearly be beneficial both in terms of the reliability of the test results obtained and in respect of reduced training costs for there to be some means of facilitating the testing process that reduces the element of operator skill required.

According to a first embodiment of the present invention there is provided ultrasonic testing apparatus comprising a base member having an aperture formed therein and a search member arranged to be rotatably received in the aperture of the base member and having at least one array aperture arranged to receive an ultrasonic array holder.

The apparatus allows a readily available ultrasonic array to be mounted within the array holder, which in turn is placed in the array aperture of the search member, thus effectively locating the ultrasonic array in a constant relationship relative to the structure to be tested, on which the testing apparatus is placed. The search member, and therefore the ultrasonic array, can then be rotated in a uniform manner within the base member.

In preferred embodiments the search member may have two or more array apertures formed therein, thus providing alternative positions or orientations of the ultrasonic array.

The or each array aperture of the search member may have a longitudinal axis that is offset from and parallel to a radius or symmetrically aligned with the centre of the search member. This provides advantages in detecting defects that extend radially from the edge of the fastener holes formed in a skin cover and/or other structure.

Preferably at least a central portion of the search member may be transparent or semitransparent. The central portion may be circular. Additionally, the central portion of the search member may include visual markings identifying the centre of rotation of the search member. These features allow the search member to be accurately located with its centre of rotation coincident with the centre of the circular fastener under investigation.

The search member may have a recess formed in its lower surface. This reduces the surface area of the search member in contact with the surface of a structure being investigated, thus reducing the friction between that surface and the search and provides clearance with any fastener heads that may protrude slightly above the inspection surface.

The apparatus may include a resilient element arranged to provide a seal between at least a portion of the apparatus and a surface upon which the apparatus is placed. The base member may include the resilient element, such as a rubber O-ring, encircling the aperture formed in the base member and arranged to form a seal between the base member and a surface upon which the base member is placed. This allows an ultrasonic coupling medium, such as an oil or gel, to be placed in the aperture before the search member is subsequently located in the base member aperture. The coupling medium improves the ultrasonic coupling between the ultrasonic array and the structure under test, as well as potentially further reducing the friction between the structure and the search member.

Figure 2A:
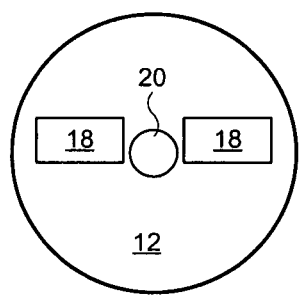
Figure 2B:
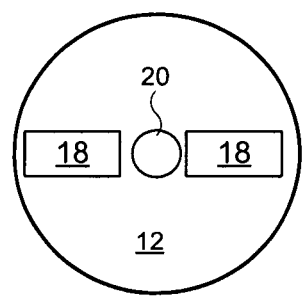
Figure 2C:
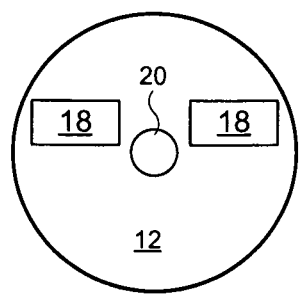
Figure 3:
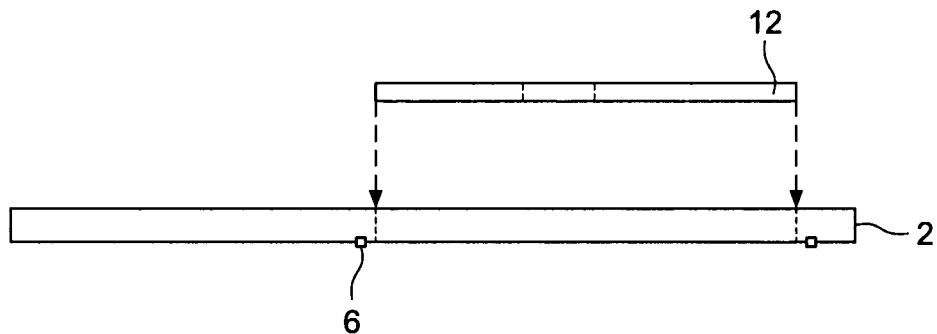
Figure 4:
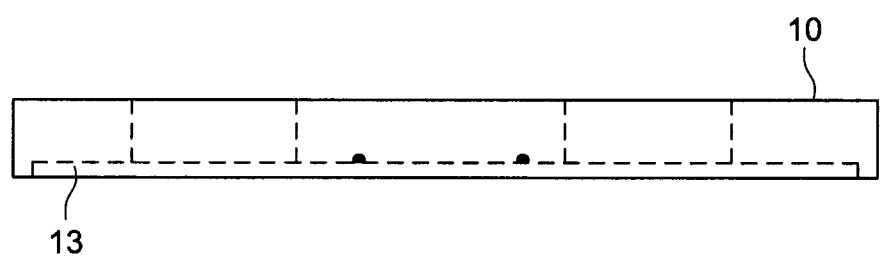
Figure 5:
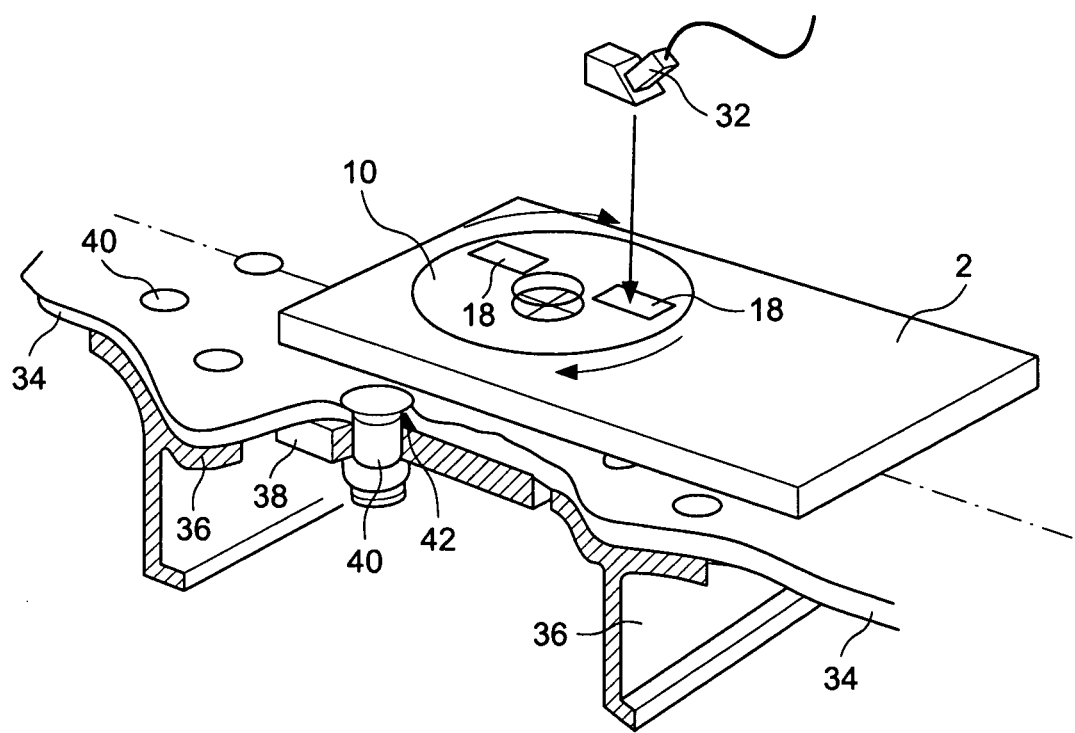

Embodiments of the present invention will now be described, by way of illustrative example only, with reference to the accompanying figures, of which:

FIG. 1 schematically illustrates in plan view a base member of the testing apparatus according to an embodiment of the present invention;

FIGS. 2a to 2c schematically illustrate in plan view a search member arranged to cooperate with the base member illustrated in FIG. 1;

FIG. 3 schematically illustrates in side elevation the base member and search member illustrated in FIGS. 1 and 2;

FIG. 4 schematically illustrates in side elevation a search member according to an embodiment of the present invention; and FIG. 5 schematically illustrates the assembled testing apparatus according to an embodiment of the present invention in use.

In an embodiment of the present invention the ultrasonic testing apparatus includes a base member 2, which is schematically illustrated in plan view in FIG. 1. The base member 2 has a circular aperture 4 formed therein extending through the thickness of the base member. Referring to FIG. 3, which shows the base member in side elevation, it can be seen that the underside of the base member 2 is substantially flat to allow the base member to placed in close contact with a flat surface of a structural element to be investigated. An annular groove is formed in the underside of the base member around the circumference of the aperture 4. A resilient seal 6, such as an O-ring is preferably located in the groove. The purpose of the O-ring will be explained subsequently. Optionally a handle 8 may be provided on the upper surface of the base member 2 to allow a user to securely hold the testing apparatus.

Referring to FIGS. 2a to 2c and 3, the testing apparatus further includes a search member 10 that includes at least a portion 12 that is circular and dimensioned to closely fit into the circular aperture 4 formed in the base member 2 such that the search member is free to rotate. In the embodiment illustrated the search member 10 comprises a disc that is substantially the same thickness as the base member 2 such that the search member is substantially flush with the upper surface of the base member. Referring to FIG. 4, the lower surface of the search member 10 may include a recess 13, preferably extending over a substantial portion of the lower surface, such that the recessed portion of the search member does not come into contact with the surface being investigated when the testing apparatus is in use, thus reducing the degree of friction between the surface and the search member. It will be appreciated that the combination of circular aperture 4 in the base member 2 and circular lower portion 12 of the search member 10 is only one possible combination. The main requirement is that the search member is constrained to rotation when located within the base member aperture. Consequently any combination of geometry that provides this constraint may be employed in embodiments of the invention.

The search member 10 includes at least one array aperture 18, the array aperture being shaped and dimensioned to receive a corresponding ultrasonic array holder of a conventional, commercially available, kind and extending completely through the full thickness of the search member. In preferred embodiments two array apertures 18 are formed in the search member. In preferred embodiments, and as illustrated in FIG. 2, the search member 10 includes at least a central section 20 that is formed of transparent of semi-transparent material and is located at the exact centre of rotation of the search member. In other embodiments the entire search member 10 may be manufactured from transparent or semi-transparent material and the central section 20 may comprise a visual marking to denote the centre rotation of the search member. The provision of such markings or transparent or semi-transparent section allows the search member, and thus entire testing apparatus, to be aligned precisely over a fastener of a structure to be tested.

FIG. 5 schematically illustrates the testing apparatus according to an embodiment of the present invention as arranged for use. The fully assembled testing apparatus comprises the base member 2 with a search member located within the aperture 4 such that the search member is free to rotate, as indicated by the arrows shown in FIG. 5. An ultrasonic array holder 22 is located within one of the array apertures 18 formed within the search member. When in use an ultrasonic array element 32 is mounted in the cavity provided in the ultrasonic array holder. The base member is placed in direct contact with an upper surface of a structure to be tested. In the example illustrated in FIG. 5, the structure under investigation comprises the top skin 34 of an aircraft wing that is fastened to respective stringers 36 and rib feet 38 by means of conventional fasteners 40. Also illustrated in FIG. 5 adjacent to the illustrated fastener 40 is the presence of a typical defect 42 that the testing apparatus is utilised to locate. By virtue of the transparent portion, and optionally the visual indicia 20, of the search member the testing apparatus is placed on the top skin of the wing such that the centre of the search member is located exactly above the fastener 40. With the ultrasonic array 32 active the search member 10, and thus the ultrasonic array and array holder, is rotated smoothly about at least one full rotation. In some embodiments it may be preferable to provide an ultrasonic coupling agent between the wing skin cover 34 and the ultrasonic array 32. This may be accomplished by adding a suitable couplant, such as a coupling gel or oil, into the aperture 4 in the base member prior to locating the search member 10 within the aperture. The couplant provides a layer between the ultrasonic array 32 housed within the array holder 22 and the wing top surface. The rubber O-ring 6 that may be provided in the base member 2 of certain embodiments of the present invention functions to retain the layer of couplant within the aperture in which the search member is located. In other embodiments, another part of the apparatus, such as the search member, may be provided with a resilient seal arranged to retain the layer of couplant within the aperture in which the search member is located.

In embodiments of the present invention in which two array apertures 18 are provided in the search member the method of operation further includes placing an array holder including an ultrasonic array in the first array aperture, rotating the search member through at least one full revolution, and if necessary subsequently relocating the array holder and array into the second of the array apertures and rotating the search member through at least one further full revolution. With reference to FIGS. 2a to 2c, it can be seen that each of the array apertures has a longitudinal axis that may or may not pass through the centre of rotation of the search member. This is to ensure that the ultrasonic beam produced by the ultrasonic array 32 is directed towards the most likely location of a typical defect, which tend to radiate radially from the hole through which the fastener passes. However, it is not uncommon for the defects to radiate tangentially from the edge of the fastener hole. By providing multi apertures for the array holder is possible for the ultrasonic beam to be directed in differing directions so as to maximise the possibility of detecting such defects.

The testing apparatus of the present invention greatly simplifies the ultrasonic testing procedure in that the positioning of the ultrasound array is simplified, thus increasing the 'Probability of Detection' (POD) of defects. By utilising the testing apparatus in combination with a phased ultrasonic array smaller defects may be located with an improved POD.

The invention claimed is:

1. Ultrasonic testing array locating apparatus comprising:
a base member having an aperture formed therein;
a search member configured to be rotatably received in said base aperture, said search member having at least one array aperture, said array aperture configured to receive an ultrasonic array holder; and
a resilient element surrounding said base aperture, said element configured to provide a seal between the base member and a substantially planar surface upon which the base member is placed and to retain a couplant in contact with a portion of said apparatus and said surface.

2. The locating apparatus of claim 1, wherein the search member has two array apertures formed therein.

3. The locating apparatus of claim 1, wherein said at least one array aperture has a longitudinal axis that passes through the center of rotation of the search member.

4. The locating apparatus of claim 1, wherein at least a central portion of the search member is one of transparent and semi-transparent.

5. The locating apparatus of claim 4, wherein the central portion of the search member includes visual indicia identifying the centre of rotation of the search member.

6. The locating apparatus of claim 1, wherein the search member has a recess formed in the lower surface of the search member.

7. The locating apparatus of claim 1, wherein said at least one array aperture has a longitudinal axis offset from and parallel to the center of rotation of the search member.

8. The locating apparatus of claim 2, wherein each of said two array apertures has a longitudinal axis that passes through the center of rotation of the search member.

9. The locating apparatus of claim 2, wherein each of said two array apertures has a longitudinal axis offset from and parallel to the center of rotation of the search member.

10. Ultrasonic testing array locating apparatus comprising:
a base member having a base aperture formed therein; and
a search member configured to be rotatably received in said base aperture, said search member having at least two array apertures configured to receive ultrasonic array holders, wherein the array apertures are arranged along a line which is offset from and parallel to the center of rotation of the search member.

11. Ultrasonic testing array locating apparatus comprising:
a base member having a base aperture formed therein;
at least one ultrasonic array holder:
a search member configured to be rotatably received in said base aperture, said search member having at least one array aperture, said array aperture having said at least one ultrasonic array holder mounted therein; and
a resilient element surrounding said base aperture, said element configured to provide a seal between at least a portion of the base member and a substantially planar surface upon which the base member is placed, said resilient element, said base member, said at least one ultrasonic array holder and said surface are configured retain a couplant in contact between a portion of said at least one ultrasonic array holder and said surface.

12. The locating apparatus of claim 11, wherein the search member has two array apertures formed therein and two ultrasonic array holders mounted therein.

13. The locating apparatus of claim 11, wherein said at least one array aperture has a longitudinal axis that passes through the center of rotation of the search member.

14. The locating apparatus of claim 11, wherein at least a central portion of the search member is one of transparent and semi-transparent.

15. The locating apparatus of claim 14, wherein the central portion of the search member includes visual indicia identifying the centre of rotation of the search member.

16. The locating apparatus of claim 11, wherein the search member has a recess formed in the lower surface of the search member.

17. The locating apparatus of claim 11, wherein said at least one array aperture has a longitudinal axis offset from and parallel to the center of rotation of the search member.

18. The locating apparatus of claim 12, wherein each of said two array apertures has a longitudinal axis that passes through the center of rotation of the search member.

19. The locating apparatus of claim 12, wherein each of said two array apertures has a longitudinal axis offset from and parallel to the center of rotation of the search member.

* * * * *